US006395268B1

(12) United States Patent
Hedrick et al.

(10) Patent No.: US 6,395,268 B1
(45) Date of Patent: May 28, 2002

(54) LYMPHOTACTIN USES

(75) Inventors: Joseph A. Hedrick, South River, NJ (US); Susan A. Hudak, Redwood City, CA (US); Donna M. Rennick, Los Altos, CA (US); Albert Zlotnik, Palo Alto, CA (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/457,501

(22) Filed: Dec. 8, 1999

Related U.S. Application Data

(63) Continuation-in-part of application No. 08/956,250, filed on Oct. 22, 1997, now Pat. No. 6,022,534.
(60) Provisional application No. 60/031,078, filed on Oct. 24, 1996.

(51) Int. Cl.[7] .................. A61K 39/395; A61K 38/19; A61K 31/00
(52) U.S. Cl. .............. 424/85.1; 424/130.1; 424/158.1; 514/2; 514/8
(58) Field of Search ............................ 424/85.1, 320.1, 424/325, 130.1, 158.1; 514/2, 8, 12

(56) References Cited

PUBLICATIONS

Marco Baggiolini and Clemens A. Dahinden, *Immunology Today*, 15(3): 127–133, 1994. "CC chemokines in allegic inflammation".
Donald M. Cook, *Journal of Leukocyte Biology*, 59:61–66, 1996. "The Role of MIP–α1 in inflammation and hematopoiesis".
Dagmar Dilloo, et al., *Nature Medicine*, 2(10):1090–1095, Oct. 1996. "Combined chemokine an cytokine gene transfer enhances antitumor immunity".
Brigitte Dorner, et al., *Journal of Biological Chemistry*, 272(13):8817–8823, 1997. "Purification, Structural Analysis, and Function of Natural ATAC, a Cytokine Secreted by CD8+ T Cells".
Bianchi Giancarlo, et al., *European Journal of Immunology*, 26:3238–3241, 1996. "Migratory response of human natural killer cells to lymphotactin".

G.J. Graham, et al., *Nature*, 344:442–444, Mar. 29, 1990. "Identification and characterization of an inhibitor of haemopoietic stem cell proliferation".
M.G. Hunter, et al., *Blood*, 86(12):4400–4408, Dec. 15, 1995. "BB–10010: An Active Variant of Human Macrophage Inflammatory Protein–α1 with Improved Pharmaceutical Properties".
Jacqueline Kennedy, et al., *J. of Immunology*, 155:203–209, 1995. "Molecular Cloning and Funtional Characterization of Human Lymphotactin".
B.I. Lord, et al., *Blood*, 79(10):2605–2609, May 15, 1992. "Macrophage Inflammatory Protein Protects Multipotent Hematopoietic Cells from the Cytotoxic Effects of Hydroxyurea In Vitro".
B.I. Lord, et al., *Blood*, 85(12):3412–3415, Jun. 15, 1995. "Mobilization of Early Hematopoietic Progenitor Cells With BB–10010: A Genetically Engineered Variant of Human Macrophage Inflammatory Protein–α1".
Azzam A. Maghazachi, et al., *FASEB Journal*, (11):765–774, Aug. 1997. "Interferon–inducible protein–10 and lymphotactin induce the chemotaxis and mobilization of intracellular calcium in natural killer cells through pertussis toxin–sensitive and –insensitive heterotimetric G–proteins".
Charlie Mantel, et al., *Proc. Natl. Acad. Sci., USA*, 90:2232–2236, Mar. 1993. "Polymerization of murine macrophage inflammatory protein 1α inactivates its myelosuppresive effects in vitro: The active form is a monomer".
Tetsuya Yoshida, et al., *FEBS Letters*, 360:155–159, 1995. "Molecular cloning of a novel C or γ type chemokine".
Byung–S. Youn, et al., *Journal of Immunology*, 155:2661–2667, 1995. "A Novel Chemokine, Macrophage Inflammatory Protein–Related Protein–2, Inhibits Colony Formation of Bone Marrow Myeloid Progenitors".

*Primary Examiner*—Elizabeth Kemmerer
*Assistant Examiner*—Regina M. DeBerry
(74) *Attorney, Agent, or Firm*—Tom Brody; Edwin P. Ching

(57) ABSTRACT

This invention relates to the use of lymphotactin or lymphotactin antagonists for administration to an animal. The administration of these therapeutic entities will attract certain cell types, or can be blocked to prevent such attraction. It also provides means to protect stem cells.

8 Claims, 12 Drawing Sheets

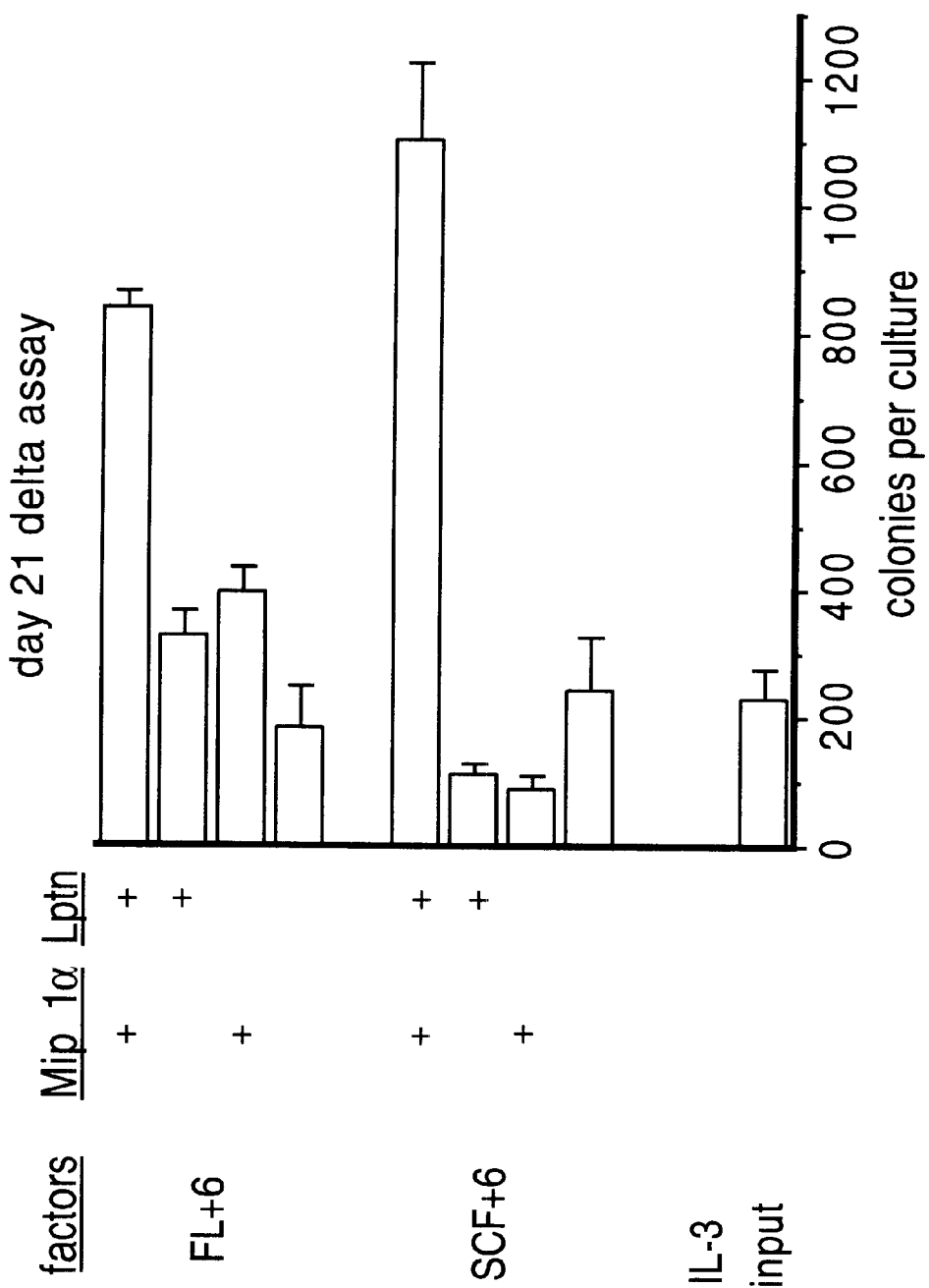

LYMPHOTACTIN USES

This application is a CIP of commonly assigned, application Ser. No. 08/956,250, filed Oct. 22, 1997, now U.S. Pat. No. 6,022,534, which is a conversion of U.S. Provisional Patent Application No. 60/031,078, filed Oct. 24, 1996, both of which are incorporated herein by reference.

FIELD OF THE INVENTION

The present invention relates to the use of lymphotactin, a recently discovered chemokine, for therapeutic administration to animal or human patients. The administration of the chemokine will attract cytotoxic T lymphocytes (CTL) and/or Natural Killer (NK) cells. In addition, the biological effects of lymphotactin can provide many of the effects of MIP-1, e.g., protecting hematopoietic stem cells from the effects of cell cycling dependent treatments, including chemotherapies and radiation therapies which specifically target cycling cells. Lymphotactin also can attact class I MHC expressing cells, e.g., which are the mediators of tissue rejection.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass..; and Paul (ed.) (1993) *Fundamental Immunology* (3d ed.) Raven Press, New York.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which should lead to significant advancements in the diagnosis and therapy of numerous medical abnormalities, e.g., immune system and other disorders.

Lymphokines apparently mediate cellular activities in a variety of ways. They have been shown to support the proliferation, growth, and differentiation of the pluripotential hematopoietic stem cells into vast numbers of progenitors comprising diverse cellular lineages making up a complex immune system. These interactions between the cellular components are necessary for a healthy immune response. These different cellular lineages often respond in a different manner when lymphokines are administered in conjunction with other agents.

The chemokines are a large and diverse superfamily of proteins generally considered a subset of the cytokines. The superfamily is subdivided into four branches, based upon whether the first two cysteines in the classical chemokine motif are adjacent (termed the "C—C" branch) or spaced by an intervening residue ("C—X—C"), or a new branch which lacks two cysteines in the corresponding motif, represented by the chemokines known as lymphotactins. See, e.g., Schall and Bacon (1994) *Current Opinion in Immunology* 6:865–873; and Bacon and Schall (1996) *Int. Arch. Allergy & Immunol.* 109:97–109. A new fourth branch is represented by a new chemokine designated CX3C chemokine.

Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modification of the effects of such factors. Thus, medical conditions where regulation of the development or physiology of relevant cells is required remains unmanageable.

SUMMARY OF THE INVENTION

This invention provides methods of increasing the numbers various lymphocytes, e.g., NK cells and cytotoxic T lymphocytes (CTL). The method comprises administering an amount of lymphotactin where said amount is effective to either attract cytotoxic T cells and/or NK cells, and/or to induce proliferation of resident cells. A preferred lymphotactin is human lymphotactin, though rat or mouse lymphotactin will function in their own, and biologically cross-reacting species. The preferred single dosage of lymphotactin is about 1 to 100 $\mu$g/kg body weight. Alternatively the amount of lymphotactin administered in a single dose is about 10–800 $\mu$g, or to reach a concentration of from pM to 1 $\mu$M of patient sera.

Alternatively, an antagonist will be effective in preventing the recruitment of such cells. This may be important, e.g., in a transplantation context, where NK and/or CTL function is harmful.

This invention also provides methods of protecting hematopoietic stem cells. The method comprises administering an effective amount of lymphotactin where said amount is effective to inhibit hematopoietic stem cell sensitivity to a cell cycle dependent cytotoxic treatment, e.g., chemotherapy and/or radiation therapy. In certain embodiments, the lymphotactin is administered in combination with another active agent, e.g., another chemokine. Such chemokines may include, e.g., MIP-1$\alpha$, MIP-1$\beta$, etc.

More particularly, the invention provides a method of increasing the numbers of NK and/or CTL cells at a location in an animal, comprising administering an amount of lymphotactin effective to increase said numbers. In preferred embodiments, the increasing is by recruitment of cells to that location; or the recruitment is to a tumor cell. Other preferred embodiments include where the tumor cell is from a solid tumor; where the increasing is by proliferation of the cells; where the increasing is of CTL cells; or where the animal is a rodent. Typically, the effective amount is between 20 and 800 $\mu$g; or the administering is parenteral.

Also provided is a method of reducing allogeneic reaction from tissue transplant in an animal, comprising a step of administering an effective amount of an antagonist of lymphotactin to the animal. Typically, the antagonist comprises an antigen binding site from an antibody which neutralizes mouse lymphotactin; the antagonist is administered at a dose of about 1–10 mg/kg body weight; or at about 1 to about 100 $\mu$g per milliliter of patient sera; or the tissue is an organ. In preferred embodiments, the antagonist reduces the influx of NK or CTL cells to the tissue; or the tissue is an organ transplant, or bone marrow transplant.

The present invention further provides a method of inducing cell cycle quiescence in a hematopoietic stem cell, comprising a step of administering to the stem cell an effective amount of lymphotactin. Preferably, the lymphotactin is a primate lympotactin; the quiescence imparts insensitivity to a cell cycle dependent cytotoxic treatment; or the treatment is a chemotherapy or radiation therapy.

Conversely, an antagonist will be effective in preventing the normal effect of natural lymphotactin, and may be useful in inducing specific hematopoietic stem cells to start cell cycling, and subsequent proliferation and/or development.

BRIEF DESCRIPTION OF THE DRAWINGS

In FIG. 1A, the wells of a microtiter plate were coated with 50 ng of either mLptn (squares) or BSA (circles) and then reacted with serial dilutions of the 4D8 rat-anti-mLptn hybridoma culture supernatant. Antibody binding was detected with HRP-conjugated mouse anti-rat IgG (1:5000 dilution) and developed with TMB peroxidase. Absorption was read at 450 nm. In FIG. 1B, for Western blotting, 3 $\mu$g of either mLptn of hLptn were electrophoresed under reducing conditions on a 4–20% gradient Tris-glycine gel. Protein was electroblotted onto Immobilon-IPVH and detected with 4D8 hybridoma supernatant (1:20 dilution) and HRP-conjugated goat anti-rat Ig. The blot was developed with ECL chemiluminescence. The molecular weights of protein markers (in kilodaltons) are indicated on the left hand side of the figure. Data are representative of at least three. separate experiments in each case.

(FIG. 6A) freshly isolated murine NK cells=21±3, IL-2 activated cells=30±4; (FIG. 6B) human NK clone 576 A6-1=58±5, 867 c20=56±3, 867 d27=49±4, and 867 c18=73±7.

(FIG. 9A) human PBLs=41±9, (FIG. 9B) murine splenocytes=67±7, (FIG. 9C) murine splenocytes=65±7.

FIGS. 10, 11, and 12 show the ability of lymphotactin, like MIP-1$\alpha$, to delay the entry of hematopoietic stem cells into cycle. These figures indicate the number of progenitor cells remaining after an initial culture period of 7, 14, or 21 days. 400 purified mouse hematopoietic Sca1$^+$, c-Kit$^+$, rhodamine$^{lo}$, lin$^-$ stem cells per culture were stimulated in the various growth factor combinations shown for 7, 14, and 21 days. At the end of the initial liquid culture period the cells were harvested, washed, and replated in methylcellulose to detect colony-forming cells (CFU-c). A combination of hematopoietic growth factors, e.g., Stem Cell Factor, IL-3, IL-6, and erythropoietin, was used in the secondary cultures to support the development of all cell lineages. Colony numbers are expressed as the mean±standard deviation for triplicate cultures. The input value indicates the number of progenitors contained in 400 cells at day 0.

DETAILED DESCRIPTION

Figure 1A:
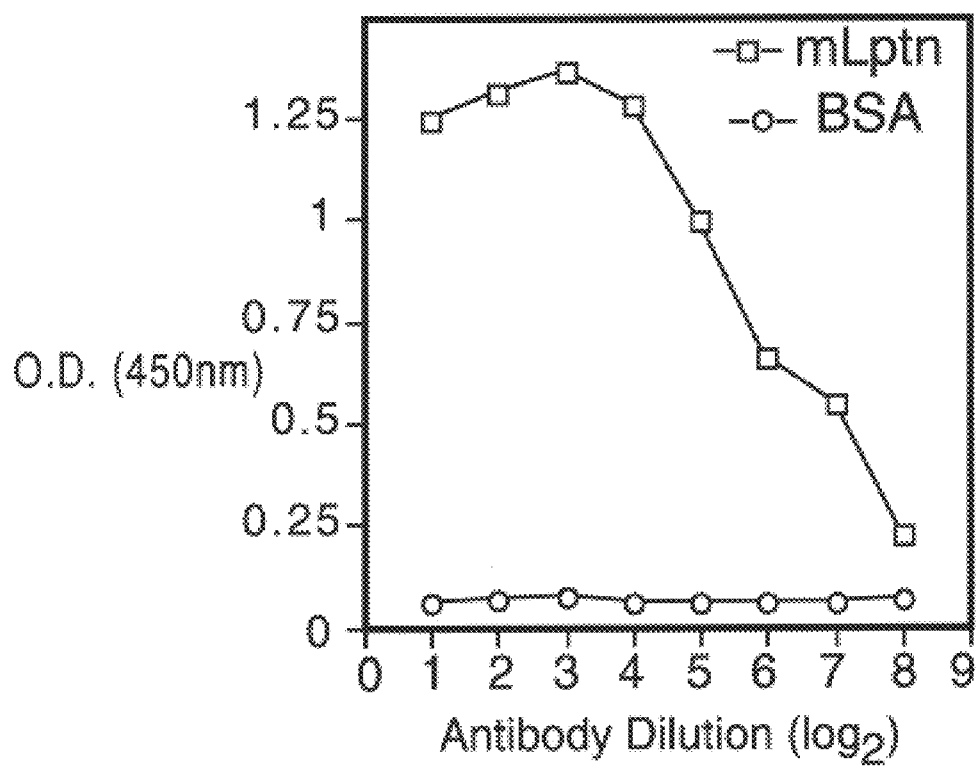
FIGS. 1A and 1B show ELISA and Western blot analysis of anti-mLptn.

This invention provides an effective means for increasing the local number of cytotoxic T cells (CTL) and/or natural killer (NK) cells. Lymphotactin, when administered, has been observed to increase the abundance of these cell types. This increase may result from attraction of said cell types, from proliferation of existing cells, or a combination of both.

Antagonists will also block such effect on such cells in circumstances, e.g., in MHC mismatched contexts, including tissue or organ rejection and graft vs. host disease, where such responses are undesireable.

In addition, lymphotactin may have positive effects on antiviral processes, whether directly by blocking a chemokine receptor used as a viral coreceptor, or to attract the NK or CTL cells attracted to sites of virally infected cells.

Lymphotactin also exhibits an activity of inducing cell cycle quiescence in hematopoietic stem cells. As such, when various drugs are administered which specifically act on proliferating cells, these stem cells are largely unaffected. Such drugs include chemotherapy reagents, e.g., nucleotide or nucleoside analogs, or radiation therapy, which mutagenizes cells which have a slowed repair process.

Mammalian lymphotactin (ltn) has been well described, e.g., in U.S. Ser. No. 08/329,704 now U.S. Pat. No. 5,786,210 and related cases, and Kelner, et al. (1994) *Science* 266:1395–1399. The preferred mammalian lymphotactin is a natural human lymphotactin.

Lymphotactin is produced in a variety of ways, both conventional and less conventional. A general review of recombinant protein production can be found, e.g., Sambrook, et al. (1989) *Molecular Cloning: A Laboratory Manual* Cold Spring Harbor Press, N.Y., or in Ausubel, et al. (Eds.; 1989 and Suppl.) *Current Protocols in Molecular Biology,* Green/Wiley, NY, N.Y. Natural sources of protein may be used as a source, and protein isolated therefrom.

Another method for preparing protein or peptides includes polypeptide synthesis methods. See, e.g., Merrifield (1988) *Science* 232:341–347; and Dawson, et al. (1994) *Science* 266:776–779.

In antagonist embodiments, the antagonist can be an antibody or fragment specific for binding to lymphotactin, e.g., which interferes with the chemokine binding to its receptor. Anti-lymphotactin reagents are produced in a variety of ways, both conventional and less conventional. A general review of antibody production can be found, e.g., in Harlow and Lane (1988) *Antibodies: A Laboratory Manual* Cold Spring Harbor Press, N.Y., or in Colligan, et al. (Eds.; 1991 and Suppl.) *Current Protocols in Immunology,* Green/Wiley, NY, N.Y. Antibodies can be polyclonal mixture or monoclonal. Antibodies can be intact immunoglobulins or fragments thereof, derived from natural sources or from recombinant sources. Antibodies also include the immunoreactive portions of intact immunoglobulins, e.g., antigen binding portions such as Fab, Fv, etc.

In brief, methods to obtain anti-lymphotactin antibodies involve administering an amount of antigen, e.g., a fragment, sufficient to induce a humoral response in a mammal. The antibodies are either collected from the mammal's sera or lymphocytes removed, immortalized, and those cell clones secreting the desired antibodies isolated and cultured for harvest of the desired antibodies.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Thymokines, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other chemotherapeutic or chemopreventive agents.

These methods require adequate sources of lymphotactin as antigens. The antigens can either be intact lymphotactin or immunoreactive peptides. Recombinant expression of lymphotactin is a convenient means for obtaining lymphotactin for use as antigens. For a general review of the applicable recombinant technology see Sambrook, et al. (1989) *Molecular Cloning—A Laboratory Manual,* Cold Spring Harbor Press, CSH, NY. Specific techniques for expressing and purifying lymphotactin are known. Expression of lymphotactin is described in PCT/US03554(WO/91/00349) and in Malefyt, et al. (1992) *Curr. Opin. Immunology* 4:314–320. Alternatively, peptide synthesis may be used to obtain intact or immunoreactive portions of lymphotactin.

The antibodies for use in this invention are preferably autologous for the patient thereby minimizing further immunological problems. Immunodeficient individuals will tend to be less reactive to non-self antibodies, and thus non-self antibodies derived from cells of the same species are also useful. Antibodies of different species are useful but means to control possible adverse immunoreactions must be undertaken. For example, humanized rat antibodies can minimize immune responses in human patients.

The antibodies for use in this invention are typically neutralizing antibodies and will preferably have binding constants which are greater than or approximates the affinity of lymphotactin for its natural receptor. Antibodies having a binding constant 100-fold less than these cytokines for their corresponding receptors are less preferred. Binding comparisons are carried out using standard equilibrium methods. The basic technology is described in Chpt 25 of Vol. 1: Immunochemistry, Ed. D. M. Weir, 4th Ed. 1986, Blackwell Scientific Publ. 25.1–25.30. Alternatively, one can use an assay for determining the molar excess of antibody which neutralizes a defined amount of IL-10 in a standard in vitro bioassay. Examples of such assays are found in Mosmann and Fong (1989) J. Immunol. Methods 116:151 (IL-4) and Fiorentino et al., 1989, J. Exp. Med. 170:2081. A reasonable range are those antibodies which neutralize a given amount of lymphotactin in a 10 to 1,000 fold excess.

The means of administration of the antagonists, e.g., αlymphotactin, are typically parenteral, preferably intravenous. The antagonists are infused into the patient using standard intravenous techniques. The antagonists are first suspended into a sterile, physiologically-compatible media, such as phosphate buffered saline. Pharmaceutically acceptable excipients such as lecithin, glucose, dextrose, antibiotics may also be included with the antagonists.

When the antagonists are antibodies, they are administered in an amount which provides circulating levels of anti-lymphotactin at about 1 to 150 $\mu$g/ml and preferably 10 to 100 $\mu$g/ml of sera for each antibody. The antibodies typically will have a 2–7 day half-life and repeated administration is necessary when levels of anti-lymphotactin are below these levels. Total amount of anti-lymphotactin applied per administration are between 1 and 10 mg/kg of body weight for each antibody.

The broad scope of this invention is best understood with reference to the following examples, which are not intended to limit the invention to specific embodiments.

EXPERIMENTAL

Example 1

In Vivo Effects: Methodology

Abbreviations used herein: Lptn, lymphotactin; mLptn, murine lymphotactin; hLptn, human lymphotactin; CT-hLptn, carboxy-terminal truncated human lymphotactin; IPTG, isopropyl β-D-thiogalactopyranoside; HRP, horse radish peroxidase; AP, alkaline phosphatase; RT., room temperature; min, minute.

Injection of lymphotactin (Lptn) into the peritoneum caused an influx of lymphocytes at 24 hours. Phenotypic analysis of the cellular influx showed that a large proportion of these cells were T lymphocytes, however, a large number of natural killer (NK) cells were also present. This effect of mLptn was specific since the cellular influx was blocked with a mLptn-specific monoclonal antibody (mAb). Similar results were observed when Lptn was injected subcutaneously and the tissue analyzed by immunohistochemistry using an anti-CD3ε mAb. Microchemotaxis assays confirmed that murine NK cells respond to mLptn and also showed human NK clones to be similarly responsive to recombinant human Lptn (hLptn). Immunohistochemical analysis of IL-2 activated murine NK cells and Northern analysis of human NK clones revealed that these cells also produce Lptn, suggesting that a self-regulatory migration mechanism exists in NK cells. Together these data confirm, in vivo, the lymphocyte-specificity of Lptn previously observed in vitro and extend its chemotactic effects to the NK cell lineage. The functional consequences of truncating the carboxy terminus of hLptn (CT-hLptn) were also investigated. This truncated molecule (which is missing the carboxy-terminal 22 amino acids of hLptn) had no detectable activity on human peripheral blood lymphocytes. In addition, while hLptn was found to attract murine splenocytes in vitro, the carboxy-terminal truncated hLptn was again inactive on murine splenocytes. This observation indicates the presence of structural features in the carboxy terminus of Lptn that are necessary for its biological activity.

The chemokines are a large family of chemoattractant cytokines whose members have been subdivided into three subfamilies on the basis of the positions of four invariant cysteines (reviewed in Baggiolini, et al. (1994) Adv. in Immun. 55:97–179; and Schall (1994) pp. 419–460, in Thomson (ed.) The Cytokine Handbook Academic Press, New York, N.Y.). The first two cysteines of the C—X—C or α chemokine subfamily are separated by a single amino acid residue, while the C—C or β chemokine subfamily members all have the first two cysteines immediately adjacent to one another. We recently described the cloning of murine Lymphotactin (Lptn) (Kelner, et al. (1994) Science 266:1395–1399) a third type of chemokine. This protein, designated the C or γ chemokine, lacks two of the four invariant cysteines ($C_1$ and $C_3$) normally found in chemokines (Kelner, et al. (1994); Kennedy, et al. (1995) J. Immunol. 155:203–209; Müller, et al. (1995) Eur. J. Immunol. 25:1744–1748; and Yoshida, et al. (1995) FEBS Lett. 360:155–159) and thus can form only one of the two intrachain disulfide bonds found in the α and β chemokines. A human form of Lptn was subsequently described (Kennedy, et al. (1995) J. Immunol. 155:203–209; Müller, et al. (1995) Eur. J. Immunol. 25:1744–1748; and Yoshida, et al. (1995) FEBS Lett. 360:155–159) which also lacks two cysteine residues. Lptn also has an extended carboxy terminus which is unusual among chemokines and further distinguishes it structurally. The gene coding for Lptn has been localized to chromosome 1 in both mouse and human, which is a different location from either the C—C or C—X—C chemokines. Lptn also differs functionally from other chemokines since it has no activity on either macrophages or neutrophils, and appears instead to be specific for lymphocytes. The in vitro chemotactic activity of Lptn has been demonstrated on both $CD4^+$ and $CD8^+$ T cells of mouse and human. Murine thymocytes, including the $CD4^-CD8^-$, $CD4^+$, and $CD8^+$ populations, also respond to Lptn. This finding is supported, e.g., by Dorner, et al. (1997) J. Biol. Chem. 272:8817–8823. A recent report has suggested that Lptn could be used in conjunction with IL-2 to enhance the antitumor activity of T lymphocytes. See, e.g., Dilloo, et al. (1996) Nature Med. 2:1090–1095. An exception are the $CD4^+CD8^+$ thymocytes which do not respond to Lptn. Binding of Lptn to either murine or human T cells has been shown to produce an intracellular $Ca^{++}$ flux similar to that observed in response to other chemokines. Finally, Lptn is also unusual in that it does not bind to the duffy antigen receptor for chemokines which can bind many C—C and C—X—C chemokines (Szabo, et al. (1995) J. Biol. Chem. 270:25348–25351.).

Expression of Lptn is essentially restricted to activated murine $CD4^-CD8^-CD3^-CD25^+CD44^+$ thymocytes (pro-T cells), from which it was originally cloned and to activated, class-I-MHC-restricted T cells, including $CD8^+$ T cells from both mouse and human and $TCR\alpha\beta^{+CD}4^-CD8^-$ T cells in mouse. A low level of expression is detectable in human $CD4^+$ T cells though it is likely that this signal arises from a human equivalent to the murine $NK1.1^+CD4^+$ T cells, which also express Lptn.

Here are reported studies of the in vivo activity of Lptn. The results of these studies confirm the previous in vitro studies in which Lptn was found to be a potent chemoattractant for T lymphocytes. In addition, it is demonstrated that Lptn attracts not only T cells, but also natural killer cells. It is shown that both murine NK cells and human NK clones respond to and produce Lptn in vitro, and that the carboxy terminus of Lptn is necessary for its activity. It is also shown that murine NK cells and human NK clones produce Lptn. Finally, the production and characterization of a neutralizing anti-mLptn mAb is described.

Cells and cell lines: Purified murine NK cells were obtained from the spleens of Rag-1$^{-/-}$ mice by Fluorescence Activated Cell Sorting (FACS) for NK1.1$^+$Gr-1$^-$ cells utilizing a FACstar flow cytometer (Becton Dickinson, Mountain View, Calif.). The purity of NK cells obtained by this method was routinely >97%. Human NK clones were the generous gift of Dr. J. Phillips (DNAX). The A3.2 T cell hybridoma was produced by fusion of BW5147 with purified $\alpha\beta$TCR$^+$CD4$^-$CD8$^-$ thymocytes using standard techniques. The resulting hybridomas were subcloned and selected for high IL-4 production, a characteristic of $\alpha\beta$TCR$^+$CD4$^-$CD8$^-$ T cells. Vicari and Zlotnik (1996) *Immunol. Today* 17:71–76.

Mice: Female CB6F1/Sim BR mice were obtained from Simonsen Laboratories (Gilroy, Calif.). Rag-1$^{-/-}$ knockout mice were obtained from The Jackson Laboratory (Bar Harbor, Me.) and have subsequently been bred and housed in a specific pathogen-free facility. Animals used were between six and ten weeks of age.

Recombinant murine lymphotactin (mLptn): The coding region of murine Lptn was subcloned into the pET-3a expression vector (Novagen, Madison, Wis.). Expression plasmids were then used to transform the BL21 (DE3) strain of *E. coli* (Novagen) containing pLys S. The transformed cells were grown in Luria broth until the O.D. at 560 nm had reached 1.0, at which point they were induced with 0.4M IPTG for an additional 4 h. The cells were then harvested by centrifugation and resuspended in 50 mM Tris (pH 7.5), 5 mM EDTA, 1 mM Pefa Bloc. Soluble protein was purified by chromatography on Q sepharose (pH 8.5; Pharmacia), SP sepharose (pH 8.5; Pharmacia), and POROS R2/M. Fractions containing mLptn were identified by migration of protein on SDS-PAGE. Fractions containing highly pure mLptn were then pooled and quantitated. The identity of the purified protein was confirmed by amino-terminal amino acid sequencing. The recombinant mLptn produced in this manner has an amino terminus sequence of MVGTEVLEQS-. The endotoxin content was <6 EU/mg of purified protein. The FLAG-murine Lptn (FLAG-mLptn) was produced as previously described in Kelner, et al. (1994) *Science* 266:1395–1399.

Recombinant human lymphotactin: Full-length recombinant hLptn was obtained from Genzyme Diagnostics (Cambridge, Mass.). The carboxy terminal truncated version of hLptn (CT-hLptn) was produced as follows: a synthetic gene encoding residues 1–71 of human Lptn was constructed with codons optimized for expression in *E. coli,* and ligated into Xba1 and Kpn1 sites of the T7-driven expression vector pCC101. CT-hLptn was expressed in a BL21 (DE3) strain of *E. coli* containing pLys S. Transformed cells were grown to an O.D., at 600nm, of between 0.7 and 1.0, at which time expression was induced with IPTG (0.5 mM). Cells were grown for an additional three hours, harvested by centrifugation, and frozen at −80° C.

The cell pellets were sonicated in 50 ml of buffer (25 mM sodium acetate, 1 mM EDTA, pH 5.0) and centrifuged (10,000 rpm, 15 min) to pellet the protein. The protein pellet was resuspended in a minimal amount of 6 M guanidine HCl and diluted into 50 volumes of sonication buffer containing 6 M urea. Soluble protein was then loaded onto a 30 ml SP Sepharose Fast Flow column, washed with 2–3 bed volumes of the loading buffer, and eluted with a 0–0.4 M gradient of NaCl. Protein-containing fractions were pooled and dialyzed against the sonication buffer at 4° C. to remove the urea. Oxidation of the single disulfide bond in the protein was accomplished by 1:1 dilution into a redox buffer (100 mM Tris, 1 mM EDTA, 2 mM oxidized glutathione, 0.2 mM reduced glutathione pH=8.0) with stirring overnight at 4° C. Final purification was achieved by reversed-phase HPLC on a Vydac $C_4$ semi-prep column. Mass spectral analysis confirmed oxidation of the cysteine residues and retention of the amino-terminal methionine.

Preparation of monoclonal anti-Lptn antibody: A male Lewis rat was immunized intraperitoneally with 25 $\mu$g of FLAG-mLptn in 1.0 ml of complete Freund's adjuvant. The rat was immunized three more times, at two week intervals, with 25 $\mu$g of FLAG-mLptn in incomplete Freund's adjuvant. Serum was collected after the third and fourth immunizations and assayed for anti-FLAG-mLptn reactivity by ELISA (described below). Four days after the last immunization the animal was euthanized and its splenocytes fused with cells, e.g., as described by Chrétien, et al. (1989) *J. Immunol. Meth.* 117:67–81. Hybridomas were initially screened against FLAG-mLptn by ELISA followed by a secondary screening against mLptn (non-FLAG). A third screening was performed to identify those hybridomas with reactivity to mLptn, as judged by Western blotting. The 4D8 anti-mLptn hybridoma was selected for cloning by these criteria and the mAb produced by this hybridoma was further characterized as having an IgG2a isotype.

In vivo experiments: Mice were injected intraperitoneally with 10 $\mu$g of purified mLptn in 200 $\mu$l of PBS (pH 7.4). Alternatively, mice were injected with 200 $\mu$l of PBS containing 10 $\mu$g of mLptn that had been preincubated with 500 $\mu$g of purified anti-mLptn mAb 4D8 or 500 $\mu$g of isotype control for 30 min on ice. Control animals were initially injected with either 200 $\mu$l PBS or 200 $\mu$l of PBS containing 10 pg of LPS (equivalent to the amount of endotoxin present in the mLptn preparation) as an endotoxin control. No differences were observed between the PBS and PBS+LPS injected animals; therefore PBS+LPS was subsequently used as a negative control. Animals were euthanized after 24 h or 72 h and the peritoneal cavity was then washed with 5 ml of ice-cold PBS. Cell counts were obtained microscopically and adjusted for the amount of PBS recovered according to the formula: adjusted cell number=total cell number× (vol. injected/vol. recovered). Cell viability was consistently above 97%.

A group of mice was injected subcutaneously in the hind footpads. Each animal was injected with 20 $\mu$l of PBS containing 1 $\mu$g mLptn in one footpad and with a PBS control containing 1 pg of LPS (an amount equivalent to the endotoxin present in the mLptn preparation) in the opposite footpad. The footpads and ankles of the mice were examined and measured with Vernier calipers twice daily for 3 days to monitor for inflammation and/or swelling. For immunohistochemical analysis, some animals were euthanized after 20–24 h and the footpads were removed and frozen in O.C.T. compound (Baxter Diagnostics Inc., McGraw Park, Ill.).

Antibodies and flow cytometric analyses: Cells obtained from peritoneal lavage were washed once in ice-cold PBS (2% FBS) and then resuspended in the same buffer for staining with the appropriate dilution of CD19-FITC, NK1.1-PE, and CD3ε-biotin, followed by streptavidin-Tricolor™. For some experiments, varying combinations of CD4-FITC, CD8-PE, Mac-1-PE, and Gr-1-biotin were also used. Flow cytometric analyses were performed on a FACScan II (Becton Dickinson) and analyzed using CellQuest software (Becton Dickinson). Antibodies used for flow cytometry were obtained commercially (PharMingen, San Diego, Calif.) as was the streptavidin-tricolor™ conjugate (Caltag, So. San Francisco, Calif.).

ELISA and western blotting: For ELISA, 50 ng of either mLptn or BSA, suspended in PBS (pH 7.2) was added to each well of a 96-well, PVC U-bottom plate (Dynatech, Chantilly, Va.) and the plate was incubated for 2 h at 37° C. The plate was then washed 3× with PBS (pH 7.2)/ 0.005% Tween-20 in a Dynatech plate washer and the supernatant from the 4D8 hybridoma was added in serial dilution. RPMI +10% FCS was used as a medium control. Following an incubation of one hour at room temperature (RT), the plate was washed again and 50 µl of horseradish peroxidase (HRP)-conjugated mouse anti-rat IgG (1:5000 dilution in PBS (pH 7.2) containing 0.005% Tween-20 and 0.1% BSA; Jackson ImmunoResearch, West Grove, Pa.) was added to each well. The plate was incubated for one hour at RT, washed again, and the assay developed using TMB-peroxidase (Kirkegaard and Perry, Gaithersburg, Md.) as a substrate. Optical density was read at 450 nm.

For Western blotting, 3 µg of either mLptn or hLptn (Genzyme) were suspended in Laemmli's buffer (containing 2% β-mercaptoethanol), boiled 5 min, and loaded onto a Tris-Glycine polyacrylamide gel with a 4–20% gradient (Novex, San Diego, Calif.). The gel was electrophoresed and protein transferred onto Immobilon-IPVH (Millipore, Bedford, Mass.) via electroblotting. The resulting protein blot was blocked overnight at 4° C. in wash buffer (0.01 M Tris, pH 7.4, 0.155 M NaCl, 0.02% Tween-20) containing 5% w/v nonfat dry milk. The blot was subsequently incubated with the 4D8 rat-anti-mLptn mAb (1:500 dilution of hybridoma supernatant) for 1.5 h, at RT. The blot was then washed 3×(5 min each wash) in wash buffer and incubated with a 1:5000 dilution of HRP-conjugated goat anti-Rat Ig (Amersham, Little Chalfont, UK) for one hour at room temp. The blot was again washed (6×, 5 min each wash) and developed with the ECL chemiluminescence detection system (Amersham) according to the manufacturer's instructions.

Immunohistochemistry: Tissue was sectioned into 5 µm slices which were thaw mounted onto organosilicone subbed slides (American Histology Reagent Co., Stockton, Calif.) and fixed by acetone immersion (5 min, −20° C.). Sections were then rinsed 3× in 0.01 M Hepes-buffered Hank's Balanced Salt Solution (Hepes/HBSS) for 5 min, each wash. Sections were subsequently blocked with 1% hydrogen peroxide, 0.2 M sodium azide in Hepes/HBSS for 20 min at RT. An additional blocking step was carried out using 10% normal goat serum in Hepes/HBSS (10 min, RT).

Following fixation and blocking, sections were incubated with hamster-anti-mouse CD3ε (PharMingen) at a concentration of 5 µg/ml in Hepes/HBSS for 2 hours at RT. The sections were washed as before and bound antibody detected with biotin-conjugated, goat-anti-hamster IgG (2.0 µg/ml in Hepes/HBSS, 1 h, RT; Vector Laboratories, Burlingame, Calif.). The sections were washed as before and final detection carried out using the Vectastain Elite ABC kit (Vector Laboratories) according to the manufacturer's instructions. Slides were then washed with Hepes/HBSS (no saponin) and developed with 3,3'-diaminobenzidine tetrahydrochloride (DAB, 0.5 mg/ml in 0.05 M Tris (pH 7.4) containing 0.0075% H202; Sigma Chemical Co., St. Louis, Mo.) as substrate. The reaction was quenched with distilled water and the sections were dehydrated in graded ethanol, immersed in xylene, and finally mounted with Permount (Fisher Scientific, Springfield, N.J.) for examination and photography.

Intracellular detection of lymphotactin: Activated A3.2 T cells were obtained by incubation of cells with RPMI 1640/10% FBS in tissue culture flasks precoated with CD3ε (PharMingen; 10 µg/ml in PBS) for 3 h. Purified murine NK cells were activated by incubation with IL-2 (500 U/ml in RPMI 1640/10% FBS) for 5 days. Following activation, cells were washed 2× in DME (no serum) and 3× in Hepes/HBSS. Cell concentration was adjusted to $1\times10^6$/ml in Hepes/HBSS and 50 µl of cell suspension ($5\times10^4$ cells) pipetted into each of the wells of an adhesion slide (Bio-Rad Laboratories, Hercules, Calif.). Following adhesion (20 min, RT), cells were fixed in 3% formalin-Hepes/HBSS (15 min, RT) and washed 2× in Hepes/HBSS. The cells were then blocked sequentially with avidin D (2 drops/ml of avidin blocking solution; Vector Laboratories) for 15 min, followed by a biotin block (2 drops/ml of biotin blocking solution; Vector Laboratories) for 15 min, a sodium azide-peroxide block (0.2 M $NaN_3$, 0.1% $H_2O_2$) for 20 min, and finally normal rabbit serum (10%) for 10 min. Blocking solutions were made in permeabilization buffer (Hepes/HBSS/0.1% saponin). The 4D8 anti-mLptn mAb was then added (5 µg/ml in permeabilization buffer) and the slides allowed to incubate for one hour at RT. The slides were washed in permeabilization buffer (3×, 5 min each wash) and incubated with a biotin-conjugated rabbit-anti-rat Ig (1:300 dilution in permeabilization buffer; Vector Laboratories) for 30 min at RT. Bound antibody was detected using the Vectastain Elite ABC kit (Vector Laboratories) and the slides developed with DAB as before.

In vitro microchemotaxis assay: The microchemotaxis assays were carried out using a modified 48-well Boyden chamber migration assay. See Bacon, et al. (1988) Br. J. Pharmacol. 95:966–974. Serial dilutions of mLptn or hLptn were made into serum free RPMI. Duplicate wells of the lower half of the microchemotaxis chamber (Neuro Probe Inc., Cabin John, Md.) were filled with the appropriate dilutions and the upper chambers of the assembly were filled with 40 µl of the appropriate cell suspension ($1-2\times10^6$ cells/ml). Data was obtained by counting five non-overlapping high-power microscope fields (400× magnification at eyepiece) from each of the wells. Cells were considered to have chemotaxed if the chemotactic index (CI=# cells migrating in experimental well/# cells migrating in media only) was greater than two.

Expression of Lptn message: Expression of Lptn mRNA by human NK clones was determined by Northern blotting. Total RNA was extracted from each clone using RNAsol (Tel-Test Inc. Friendswood, Tex.) according to the manufacturer's instructions. Northern blotting was performed by standard methods using 10 µg of total RNA from each clone.

Example 2

Characterization of an Anti-mLptn mAb

Figure 1B:
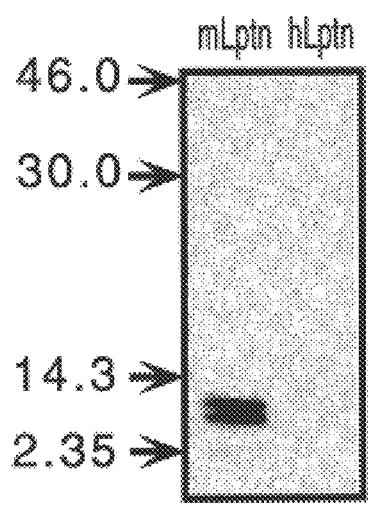
Figure 2:
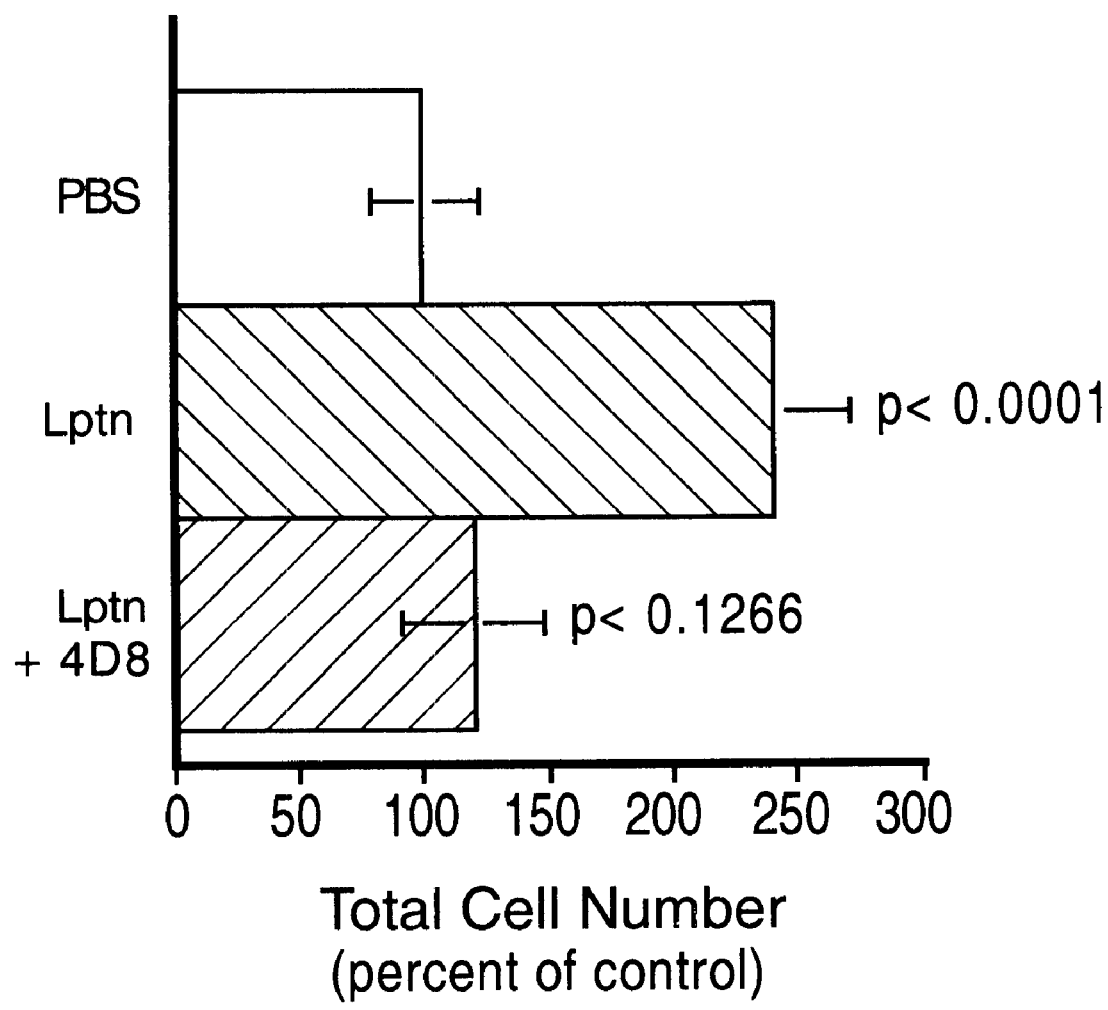
FIG. 2 shows an influx of cells into the peritoneal cavity in response to Lptn. Mice were injected intraperitoneally with 200 $\mu$l of PBS containing 10 pg of LPS, 200 $\mu$l of PBS containing 10 $\mu$g of mLptn, or 200 $\mu$l of PBS containing 10 $\mu$g of mLptn and 500 $\mu$g of purified 4D8 mAb. The mice were euthanized after 24 hours and peritoneal lavage collected and total cell numbers calculated. The results shown are representative of seven separate experiments (three using the 4D8 mAb) consisting of five mice/condition/ in each experiment and are expressed as a percent of the PBS+LPS control (100%).
Figure 3:
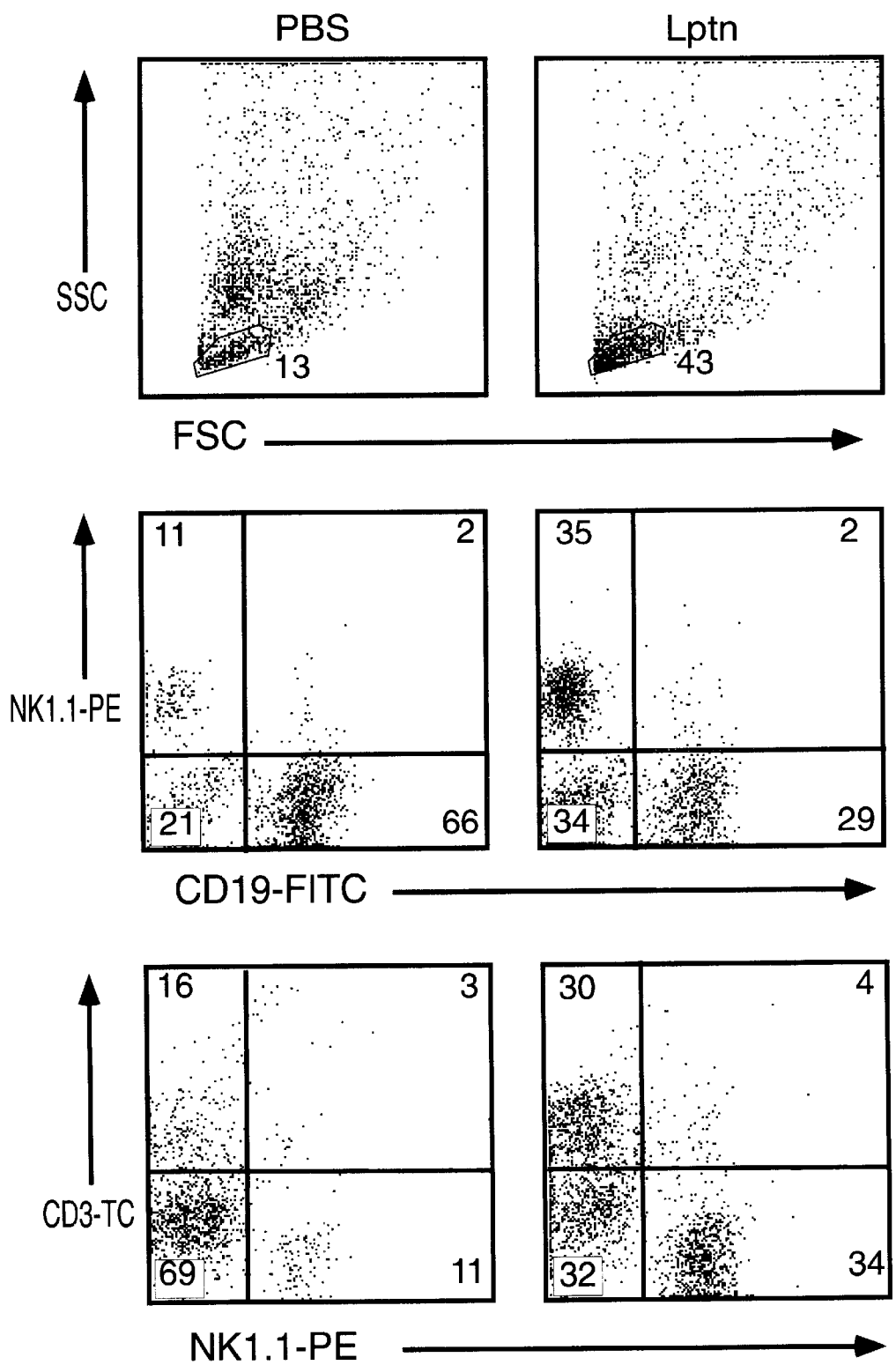
FIG. 3 shows flow cytometric analysis of cells migrating in response to Lptn. Cells recovered from the peritoneal lavage of PBS-injected mice (left column) or mLptn-injected mice (right column) were analyzed by flow cytometry. Electronic gates were placed around cells with a lymphocyte scatter profile and $3 \times 10^5$ cells analyzed using FITC-conjugated CD19 (1:200 dilution), PE-conjugated NK1.1 (1:100 dilution), and biotin-conjugated CD3 (1:1000) antibodies. Biotin-conjugated CD3 was detected with streptavidin-TriColor™. The results shown are representative of seven independent experiments, each consisting of five animals/condition.
Figure 4:
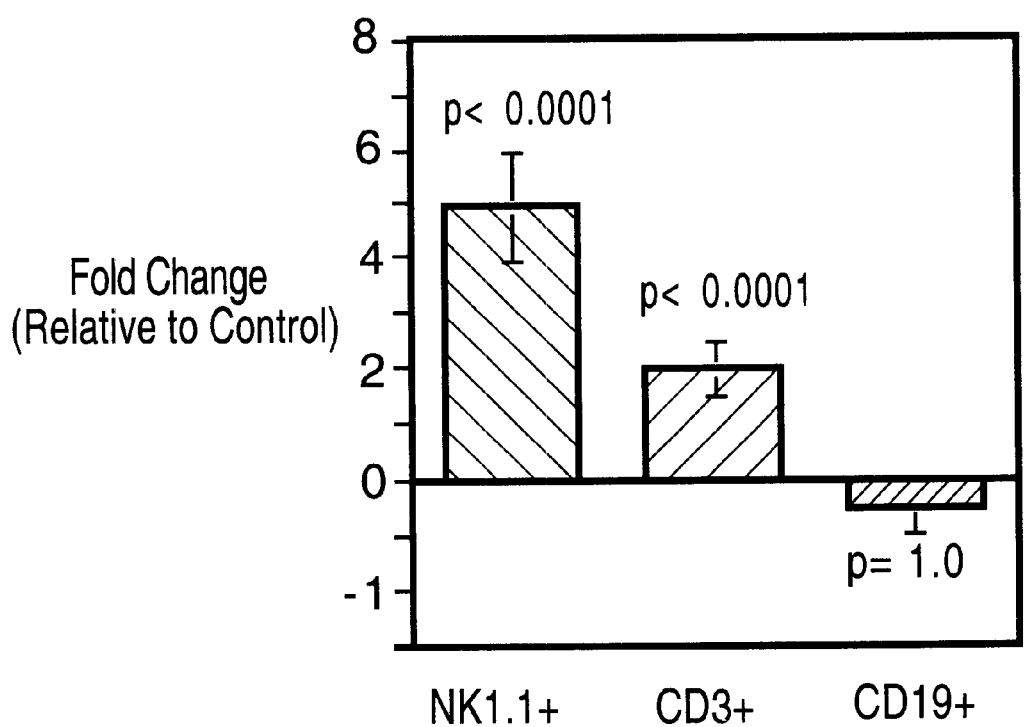
FIG. 4 shows changes in absolute numbers of peritoneal lymphocyte populations (NK, T, and B cells) as a result of mLptn injection. The average change in the absolute number of each lymphocyte population was determined for each of seven independent experiments and normalized to the average control values for that particular experiment. The data were then combined to produce the figure displayed. Results are expressed as percent increase or decrease relative to the PBS control. Each independent experiment contained five animals/condition.
Figure 5:
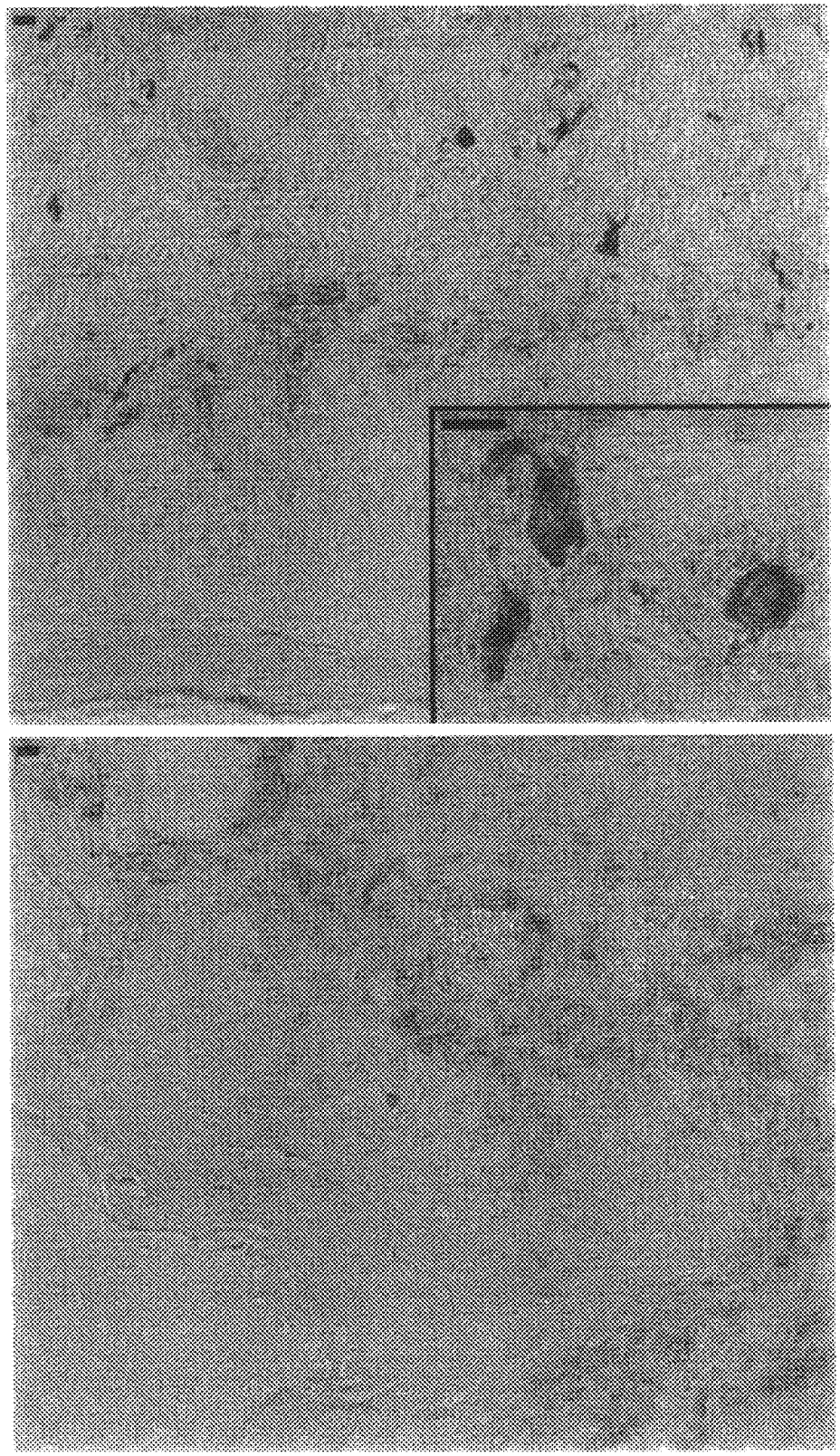
FIG. 5 shows infiltration of T cells in response to subcutaneous injection of Lptn. Frozen sections from the rear footpads of mice that had been subcutaneously injected with either PBS (top panel) or PBS containing 1 $\mu$g of mLptn (bottom panel, bottom panel inset) were analyzed by immunohistochemistry using the CD3$\epsilon$ mAb. Bound CD3$\epsilon$ was detected with biotin-conjugated goat anti-hamster IgG and the Vectastain Elite ABC kit. Stained sections were developed with DAB. Results shown from one out of two independent experiments. Bars are 5 $\mu$m.
Figure 6A:
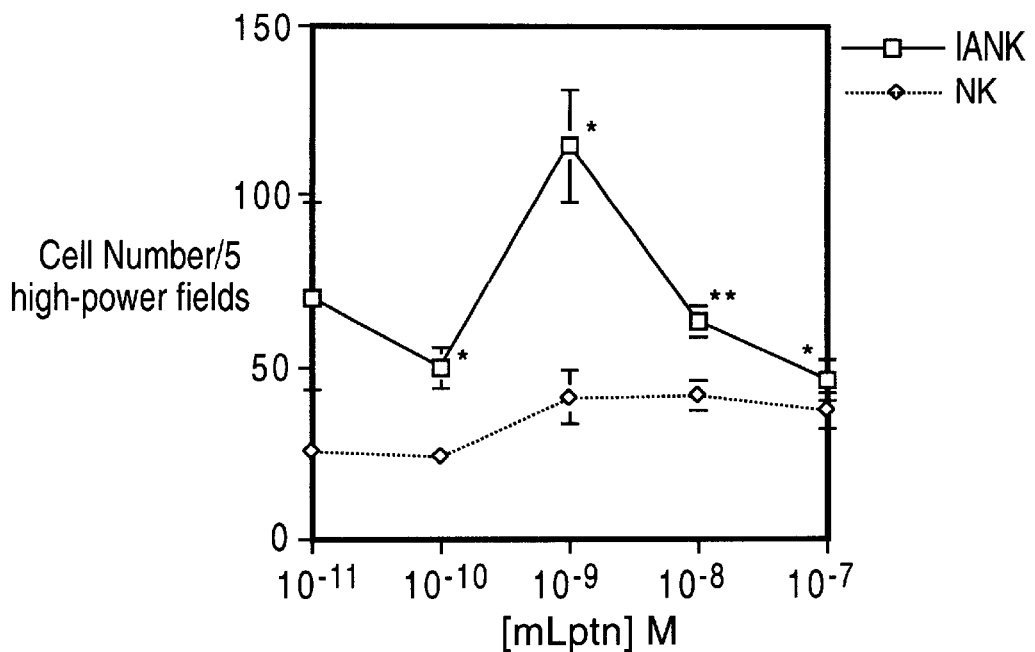
FIGS. 6A and 6B show in vitro chemotaxis of NK cells in response to Lptn. Microchemotaxis assays were conducted for (FIG. 6A) murine NK cells and (FIG. 6B) human NK clones responding to mLptn or hLptn, respectively. Migration is expressed as cell number per five high power (400×) fields, with duplicate wells counted for concentration of Lptn, versus molar concentration of Lptn. Background migration in media alone.
Figure 6B:
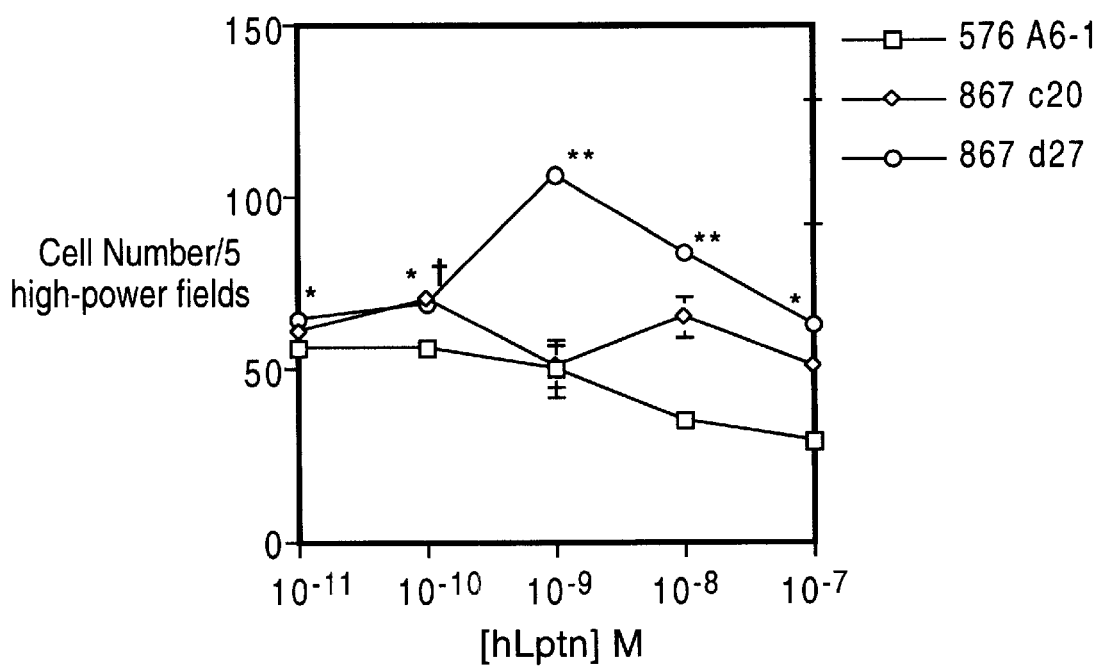
Figure 7A:
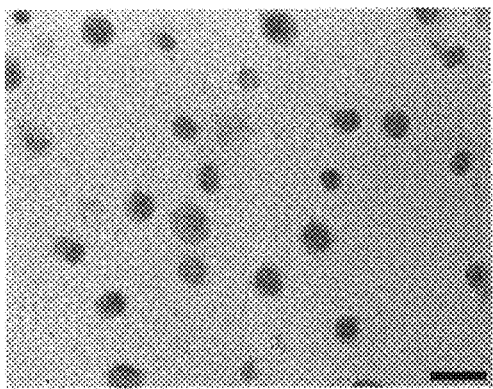
FIGS. 7A, 7B, 7C, and 7D shows expression of Lptn by murine NK cells. CD3-activated A3.2 T cells (control, A & B) or IL-2-activated NK cells (C & D) were fixed in formalin and stained intracellularly with the 4D8 anti-mLptn mAb (A, B & D) or an isotype control antibody (C). Bound antibody was detected with biotin-conjugated goat anti-rat IgG and the Vectastain Elite ABC kit. Slides were then developed with DAB. Bars are 5 $\mu$m.
Figure 7B:
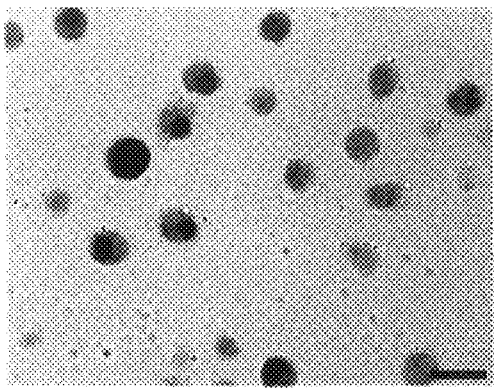
Figure 7C:
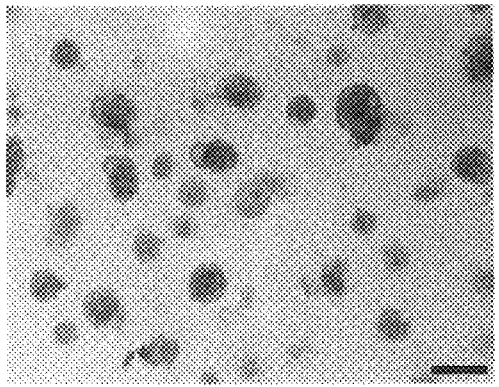
Figure 7D:
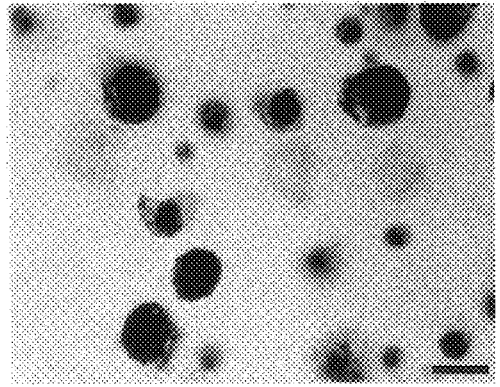
Figure 8:
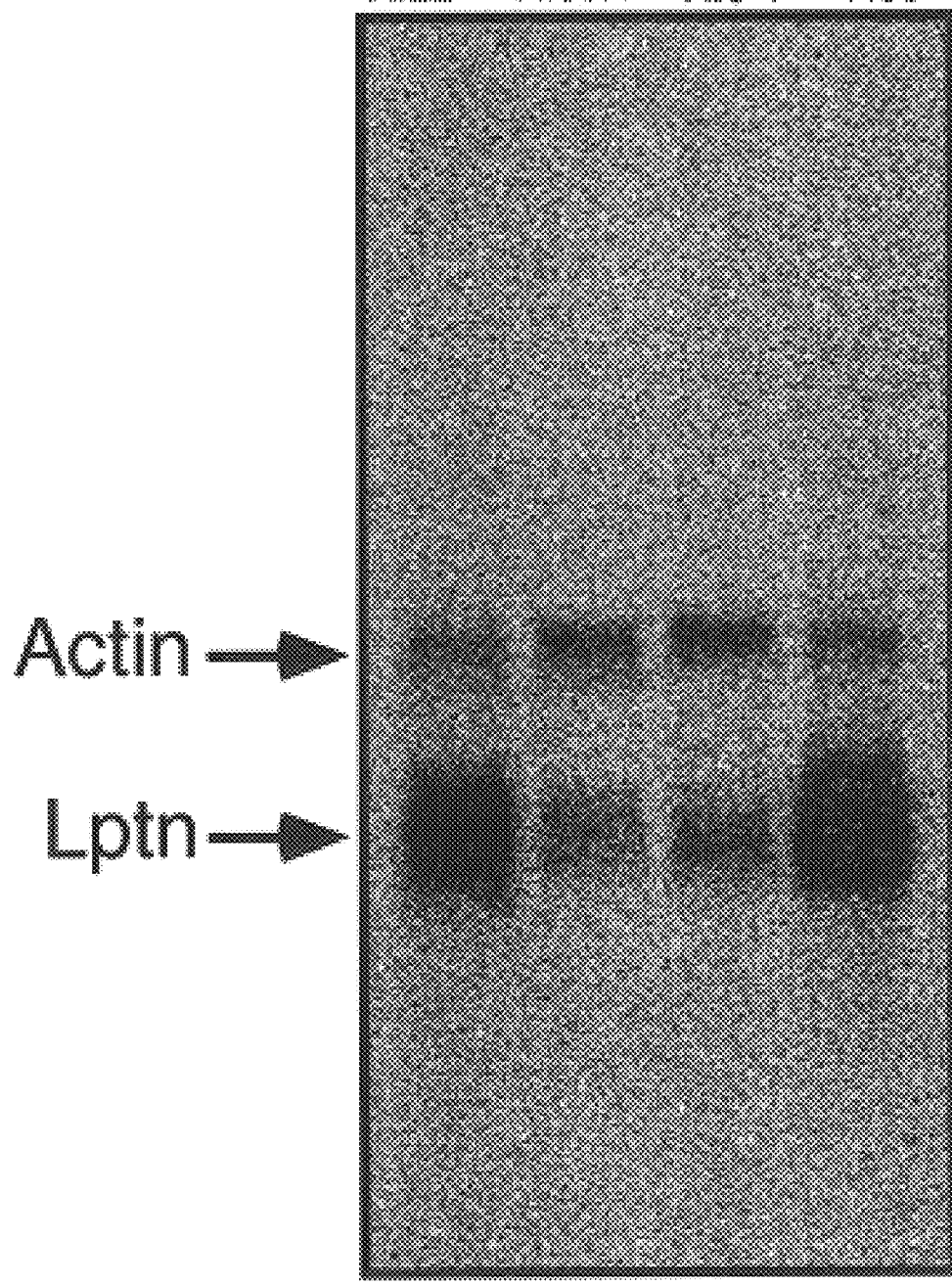
FIG. 8 shows expression of Lptn mRNA by human NK clones. 10 $\mu$g of total RNA from each of four human NK clones was analyzed by Northern blotting using human Lptn as a probe. The blot had been previously probed with actin as a control for equal loading of RNA. The mRNAs for actin and Lptn are indicated.

Anti-Lptn mAbs were raised in Lewis rats by immunization with purified recombinant FLAG-mLptn. Hybridomas produced from the splenocytes of immunized animals were then screened by ELISA for reactivity with FLAG-mLptn. The hybridomas which were positive in this initial screen were then tested for ELISA reactivity against non-FLAG mLptn in order to eliminate any hybridomas which were reactive with the FLAG peptide. Those hybridomas with ELISA reactivity to mLptn were then screened for their ability to recognize mLptn in Western blotting. One hybridoma designated 4D8, identified through this screening procedure, exhibited strong reactivity with mLptn by ELISA but did not score with the Bovine Serum Albumin protein control (FIG. 1A). Furthermore, 4D8 reacted with purified recombinant mLptn by Western blotting but was unreactive with full-length hLptn (FIG. 1B). Taken together, these data indicate that the 4D8 mAb specifically recognizes mLptn.

Example 3

Intraperitoneal Injection of Lptn Causes an Influx of Cells

The in vitro chemotactic activity of mLptn on murine thymocytes and mature murine T lymphocytes has been described. In order to confirm this activity in vivo, mLptn was injected into the peritoneal cavity of female CB6F1 mice. Initially, doses of 1 μg and 5 μg of Lptn were used, however, no effect was observed following injection of 1 μg and the effects were marginal with 5 μg. A strong influx of cells into the peritoneum was observed, however, when 10 μg of Lptn were injected. This response was evident at 24 hours, but had largely disappeared by 72 hours post-injection. This cellular influx into the peritoneum was not observed in control animals injected with an endotoxin-matched (10 pg LPS) PBS control. Furthermore, this effect was abolished when 0.5 mg of the anti-mLptn mAb 4D8 was co-injected with 10 μg mLptn.

Example 4

NK cells and T Cells are Attracted by Lptn in vivo

Cells recovered from the peritoneum of mice injected 24 hours previously with mLptn were analyzed by FACS to determine what type of cells were attracted. The cells recovered from the mLptn-injected mice showed a marked increase in the percentage of cells matching the known scatter profile of lymphocytes. This population was found to be significantly enriched for T cells (CD3$^+$NK1.1$^-$), as was expected. Surprisingly this population was also enriched for NK cells (NK1.1$^+$CD3$^-$). Although the percentage of B cells (identified as CD19$^+$CD3$^-$ cells) in the peritoneal lymphocyte population was reduced, the absolute number of B cells, based on the percentages obtained by FACS and the total number of cells recovered from the peritoneum, was not significantly affected. The absolute numbers of NK cells in the peritoneum of Lptn-injected mice increased about 5-fold while the absolute number of T cells increased about 2-fold. In some experiments the CD4:CD8 phenotype of the CD3$^+$ cells was also examined, however, the relative ratio of CD4:CD8 (approx. 1.2:1) observed in the Lptn-injected mice as compared to control animals was not significantly different (see Table 1). In contrast, the absolute number of macrophages (Mac-1$^+$ cells) present in the peritoneum did not show a significant change in mLptn-injected animals.

This finding is confirmed, e.g., in Giancarlo, et al. (1996) *Eur. J. Immunol.* 26:3238–3241; and Maghazaci, et al. (1997) *FASEB J.* 11:765–774.

Example 5

Subcutaneous Injection of mLptn Attracts T Lymphocytes

We sought to confirm the ability of Lptn to attract T lymphocytes in vivo by utilizing a subcutaneous injection model. In this model, mice were injected in one footpad with a PBS control, while the other footpad received an injection of 1 μg of mLptn. The animals were sacrificed after 24 h, the footpads excised, and analyzed by immunohistochemistry. Serial sections from the PBS-injected footpads showed no significant staining with the anti-CD3ε mAb used while the footpads receiving mLptn showed numerous cells with anti-CD3ε reactivity. Interestingly, at no time did any animal show signs of inflammation in either the PBS- or mLptn-injected footpads.

Example 6

Lymphotactin attracts NK cells in vitro

In vitro microchemotaxis assays were performed on purified murine NK cells in order to confirm their in vivo Lptn-responsiveness that had been observed for these cells. Murine NK cells (NK1.1$^+$Gr-1$^-$) were isolated from Rag-1$^{-/-}$ deficient mice in order to insure that contamination of the NK cells by other lymphocyte populations, particularly NK1.1$^+$CD3$^+$ T cells, would not be a concern. The freshly isolated NK cells were either tested immediately in the microchemotaxis assay or were activated with IL-2 for 5 days and then examined for chemotaxis to mLptn. The IL-2 activated NK cells were responsive to Lptn in vitro with a peak response around $10^{-8}$ M. Freshly isolated NK cells, however, were found to be unresponsive to mLptn in these assays. See also, e.g. Giancarlo, et al. (1996) *Eur. J. Immunol.* 26:3238–3241; and Maghazaci, et al. (1997) *FASEB J.* 11:765–774.

Example 7

Chemotaxis of Human NK Cell Clones

Because murine NK cells were chemotactic in response to Lptn it was useful to determine whether human NK cells would be similarly responsive. To address this question, several human NK clones were examined for their ability to respond to hLptn in the microchemotaxis assay. Some NK clones were found to respond very well while others showed little or no response. The clones which did respond displayed a similar dose-response to that observed with murine NK cells, with a peak response around $10^8$ M. Altogether, two of seven human NK clones examined showed significant Lptn responsiveness (i.e., a chemotactic index of 2 or more).

Example 8

NK Cells Produce Lymphotactin

Since NK cells were found to respond to Lptn, it was of interest to determine whether or not these cells could also make Lptn. In order to demonstrate that murine NK cells express Lptn, the 4D8 anti-mLptn mAb was used for intracellular staining. While no staining of IL-2 activated murine NK cells was detected with an isotype control antibody, intracellular staining with the 4D8 mAb was easily detected. Since murine Lptn mRNA had previously been found to be expressed in murine αβTCR$^+$CD4$^-$CD8$^-$ thymocytes, the A3.2 αβTCR$^+$CD4$^{-CD}$8$^{31}$ thymocyte hybridoma was examined as a control for expression of Lptn. A3.2 cells which had been activated on solid phase anti-CD3ε for 3 hours showed a pattern of intracellular staining similar to that of the IL-2 activated murine NK cells. The isotype control for these cells was similarly negative. Neither freshly isolated NK cells nor unactivated A3.2 cells showed staining for Lptn.

Human NK clones were also examined for expression of Lptn. Since no antibody to hLptn is presently available, a panel of human NK clones were analysed for expression of Lptn message. Total RNA was extracted from a series of human NK clones and subjected to Northern blotting with a probe corresponding to the coding sequence of human Lptn. A signal of the appropriate size was observed in each of the clones examined, although the intensity of the signal varied from clone to clone. An actin probe, used as a control, demonstrated equivalent mRNA loading.

Figure 9A:
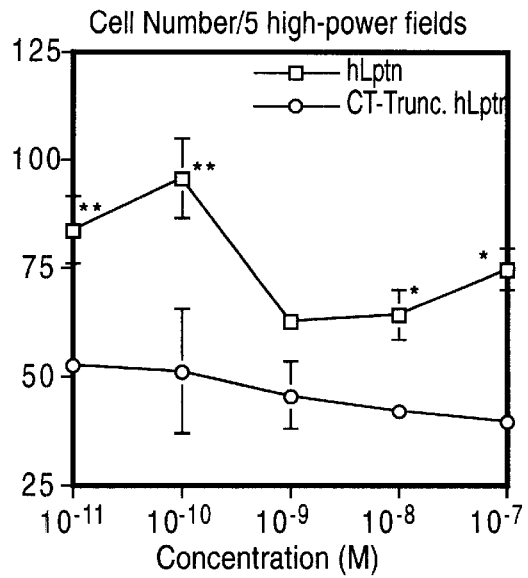
FIGS. 9A, 9B, and 9C show that human PBLs and murine splenocytes fail to respond to CT-hLptn. Microchemotaxis assays were conducted with either (FIG. 9A) human PBLs or (FIGS. 9B & 9C) murine splenocytes using (FIGS. 9A & 9B) full length hLptn (squares) and CT-hLptn (circles) or (FIG. 9C) mLptn. Migration is expressed as cell number per five high power (400×) fields, with duplicate wells counted for concentration of Lptn. Background migration in media alone.
Figure 9B:
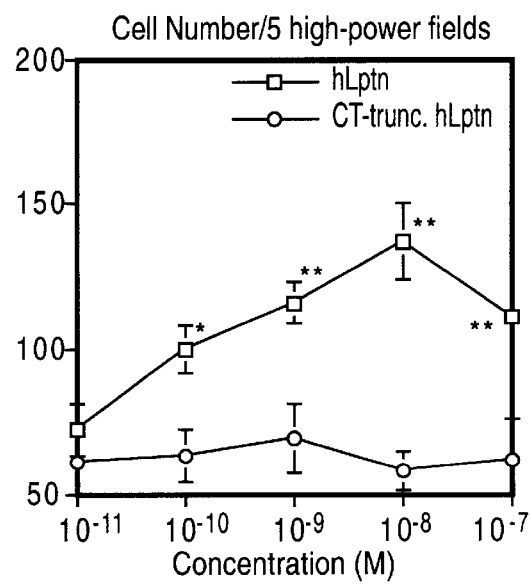
Figure 9C:
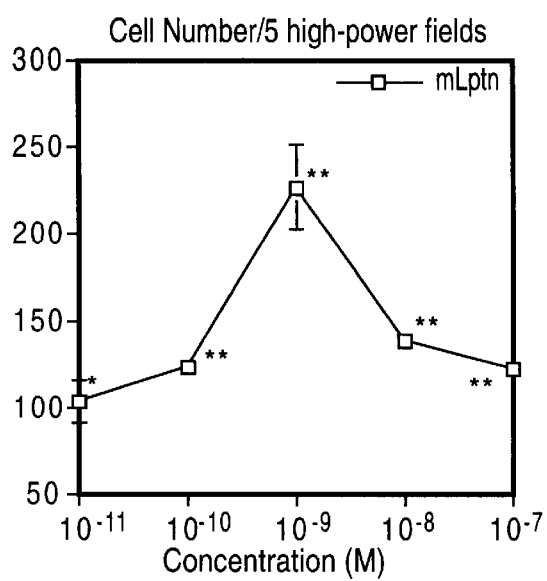

Example 9
Carboxyl-terminal Truncated Lymphotactin Lacks Chemotactic Activity As discussed above, Lptn has an unusually long carboxy-terminal tail extending approximately 22 amino acids beyond the last amino acid of most C—C chemokines. A truncated version of human Lptn, lacking the carboxy-terminal 22 amino acids (CT-hLptn), was produced as part of an effort to understand the structure of lymphotactin. We took advantage of the existence of this truncated molecule in order to investigate the role that the tail plays in the activity of Lptn. The activity of the CT-hLptn protein on human PBLs was compared with that of full length hLptn in the microchemotaxis assay. The truncated protein was found to lack detectable activity (FIG. 9A) when compared with full-length hLptn. Human and mouse Lptn have considerable similarity at the amino acid level, particularly in the carboxy-terminal 22 amino acids, so the ability of hLptn to attract murine lymphocytes was also investigated. For this series of microchemotaxis assays murine splenocytes were utilized which have previously been shown to respond to Lptn. Full length hLptn was found to attract murine splenocytes although the dose response was shifted, with a peak at $10^{-7}$ M hLptn, as compared to the $10^{-8}$ M peak obtained with mLptn. The CT-hLptn lacked chemotactic activity for murine splenocytes, in accordance with the findings obtained using human PBLs.

The ability of Lptn to attract lymphocytes in vitro has been previously reported. It is, however, important to study the effects of chemokines in vivo. Here, a novel activity for lymphotactin is described, namely the ability to attract NK cells, and confirm in vivo that Lptn is capable of recruiting T lymphocytes. Intraperitoneal injection of Lptn causes a significant influx of NK cells as well as T lymphocytes. This influx of T and NK cells was specific as it was inhibited by co-injection of the anti-mLptn mAb, 4D8. Similarly, subcutaneous injection of Lptn causes an influx of T cells, confirming that this protein has the T cell chemotactic properties in vivo that have been observed in vitro.

The observation that Lptn chemoattracted NK cells in vivo was an unexpected result. NK cell chemotaxis in vitro using microchemotaxis assays was demonstrated. Interestingly, freshly isolated NK cells fail to respond to mLptn in vitro, while activated NK cells were found to respond very well. NK cells recovered from the peritoneum of mLptn-injected mice were evaluated for expression of Ly49 and CD69, two markers associated with NK activation, but no significant expression of these molecules was observed, suggesting that these cells were not activated. Other investigators have obtained similar in vitro results with freshly isolated versus IL-2 activated NK cells. See, e.g., Allavena, et al. (1994) *Eur. J. Immunol.* 24:3233–3236; and Maghazachi, et al. (1994) *J. Immunol.* 153:4969–4977. Taub et al. (1995) *J. Immunol.* 155:3877–3888, however, have reported that fibronectin coating of the porous filters utilized in the microchemotaxis assays allows migration of freshly isolated NK cells. Another possible explanation for the increase in peritoneal NK cells is that Lptn is expanding a pool of NK cells already present in the peritoneum. No effect of Lptn on proliferation of NK, either in the presence or absence of exogenous IL-2, was observed, suggesting that this is unlikely. Taken together, these observations strongly suggest that Lptn recruits NK cells in vivo.

It was also investigated whether human NK cells might be similarly responsive to Lptn. Some, but not all, human NK clones were found to respond to hLptn in microchemotaxis assays. This further confirms the NK cell response to Lptn and demonstrates that human Lptn exhibits similar properties to murine Lptn. The varying ability of human NK clones to respond to lymphotactin may reflect clone-specific differences in receptor expression or in the relative mobility of particular clones. Alternatively, since these clones are maintained in culture by constant restimulation, their ability to respond to chemotactic stimuli may depend on how recently they had been stimulated.

Although a number of chemokines have been reported to attract NK cells in vitro, this may be the first report demonstration that a chemokine is capable of attracting NK cells in vivo.

In addition to the NK cell chemotactic response to lymphotactin, it was also found that both IL-2 activated murine NK cells and human NK cell clones express Lptn protein or Lptn message, respectively. This raises the possibility that an activated NK cell could recruit other NK cells or T lymphocytes to the site of an infection or into a tumor mass. Indeed, Lptn message has been reported to be rapidly up-regulated in activated T cells and here it is observed that protein can be expressed by the A3.2 thymocyte hybridoma within three hours of activation, indicating that Lptn protein is produced shortly after the appearance of its mRNA.

As previously mentioned, one of the structural features which distinguishes Lptn from other chemokines is the unusually long carboxy-terminus of Lptn, that is highly conserved (68.2% identity in the last 22 amino acids) between mouse and human proteins. It was investigated whether this extended "tail" was necessary for Lptn's function by examining the activity of a carboxy-terminal truncated version of the human protein. This truncation removes the carboxy-terminal 22 amino acids of Lptn and results in a protein that is similar in size to other chemokines. The ability of CT-hLptn to cause chemotaxis of human peripheral blood lymphocytes was evaluated. In contrast to the full-length hLptn, which showed clear chemotactic activity for human PBLs, the CT-hLptn was completely inactive. Similarly, while the full-length hLptn was active on murine splenocytes, the truncated version was once again inactive. The results of these experiments demonstrate that the carboxy terminus of Lptn is indeed critical to at least these functions. This is in contrast to the data obtained with the murine chemokine JE, which also possesses an extended C-terminus. Truncation of the extended tail of that protein does not significantly affect is biologic activity. One possible explanation for these differences is that the C-terminus is directly or indirectly involved in binding to the Lptn receptor. Another possibility is that because Lptn lacks two of the four cysteine residues normally found in chemokines (and must therefore also lack one of the two disulfide linkages present in most C—C and C—X—C chemokines) the extended carboxy-terminal tail is needed to stabilize the protein's structure. Both the C—C and C—X—C chemokines have been shown to possess a carboxy-terminal α-helix. See, e.g., St. Charles, et al. (1989) *J. Biol. Chem.* 264:2092–2099; Clore, et al. (1990) *Biochemistry* 29:1689–1696; and Baldwin, et al. (1991) *Proc. Natl. Acad. Sci. U.S.A.* 88:502–506. It is reasonable to believe that the truncation of the carboxy-terminal 22 amino acids disrupts the predicted carboxy-terminal α-helix of lymphotactin and similarly destroys its biologic activity.

Previous work has also demonstrated that amino-terminus of the C—C and C—X—C chemokines is very sensitive to modification and that even minor changes can result in the loss of their chemotactic activity. See Zhang, et al. (1994) *J. Biol. Chem.* 268:15918–15924; and Gong and Clark-Lewis (1995) *J. Exp. Med.* 181:631–640. In contrast to this, the murine Lptn with a amino-terminal FLAG sequence is active. This contrasts with the C—C chemokine MCP-1, which loses biologic activity if an amino-terminal FLAG is added to its sequence. In this report another version of mLptn with an amino-terminal methionine residue is active in vitro and in vivo. These data suggest that the biologic activity of Lptn is retained even after alterations in its amino-terminus. The structures of the full length and carboxy-terminal truncated hLptn are currently being determined and this information will certainly shed some light on the structure-function relationship of lymphotactin.

Lymphotactin is an important chemokine, not only because of its unique structure and chromosomal localization, but also because it represents, with the possible exception of the monokine induced by interferon-γ (Mig) (Liao, et al. (1995) *J. Exp. Med.* 182:1301–1314) the only lymphocyte-specific chemokine. The present invention shows that the lymphocyte specificity of Lptn is observed in vivo. The characterization of Lptn in vivo has also uncovered a novel activity for Lptn, namely chemoattraction of NK cells, which in turn suggests the possibility for anti-viral and anti-tumor effects. The data discussed herein shows that the NK activity for Lptn observed in mice also applies to hLptn and human NK cells. The development of a neutralizing anti-Lptn mAb is also described.

|  | CD4:CD8 | |
|---|---|---|
|  | PBS | Lptn |
| Experiment 1: | 58.2%:40.2% | 48.3%:42.9% |
| Experiment 2: | 51.4%:45.7% | 52.1%:44.3% |

Table 1. The CD4 and CD8 phenotype of $CD3^+$ peritoneal lymphocytes. The percent $CD4^+$ or $CD8^+$ cells was determined by FACS analysis of peritoneal lymphocytes harvested from PBS injected control mice or Lptn-injected mice and gated on $CD3^+$ cells. Cells were stained with FITC-conjugated CD4, PE-conjugated CD8, and biotin-conjugated CD3. Bound biotin-CD3 was detected with streptavidin-TriColor™.

Example 10
Lymphotactin and Tissue Rejection; Graft vs. Host Disease

The expression pattern of Lptn is highly specific. The cells that produce Lptn include: NK cells, dendritic epidermal γδ T cells, and class I restricted T cells. Dendritic cells may produce Lptn as well. Of this list, by far the most important producers, in terms of numbers, are the class I restricted T cells. Furthermore, Lptn is a very early and important product of these cells following activation. These cells play a critical role in various immune responses, including immunity to tumors as well as organ rejection.

The cells recruited by Lptn in vivo have been studied. These include what are likely to be subsets of CD4 and CD8 T cells, but the biggest change (as a percentage) is observed in the NK compartment, where there is a 5–10 fold increase in the number of NK cells. Taken together, these observations imply that Lptn likely plays an important role in the modulation of these responses. As such, it is likely that: (a) Lptn constitutes an early recruiting signal for class I restricted T cells, as well as for NK cells. Thus, Lptn would be necessary for the development of these immune reponses, since failure to recruit these cells would abrogate them. (b) Interference with this normal early'signaling mechanism would result in a significant reduction in the magnitude of these immune responses. One important process where early activation of class I-restricted T cells, as well as NK cells, is critical is in the process of tissue or organ rejection, or in graft vs. host disease. Thus, it is likely that neutralization of Lptn, e.g., using a monoclonal antibody antagonist or a mutein antagonist, will result in modulation of the fate of the transplant across MHC differences. (c) The presence of Lptn in a tumor would result in the recruitment into the tumor mass of cells capable of destroying the tumor cells, including CD4 and CD8 T cells as well as NK cells.

Example 11
Hematopoietic Effects of Lymphotactin $Lin^-$ $Sca-1^+$ $rhodamine^{lo}$ $c-kit^+$ stem cells were isolated. These cells were incubated for at 37° C. and 5% $CO_2$ in 1.5 ml eppendorf tubes at 400 cells per 400 µl. Growth factors, alone or in appropriate combinations, were added to the Iscove's Modified Dulbecco's Medium (IMDM)+15% fetal bovine serum (FBS)+penn-strep+HEPES at a final concentration of 50–100 ng/ml, in the 400 µl/tube.

At day 7, an aliquot of each culture which is ¼ of the input volume is withdrawn and the culture is refed with 200 µl of growth factors in IMDM+15% FBS. 5 µl is withdrawn from the sample and counted.

The remaining cells were diluted with IMDM+15% FBS and underlayed with FBS. The culture was spun at 1000 RPM for 5 min. The supernate is aspirated and the cells resuspended in 100 µl IMDM+15% FBS.

CFU-c assays were set-up to contain IL-3+IL-6+SCF+epo. The cells from each delta culture were added to a single set-up along with methylcellulose (final conc 0.8%). The contents of each set-up were mixed with a 3 ml syringe and 16 Ga needle and plated into three 35 mm pertri dishes. Cultures were incubated at 37° C. and 5% $CO_2$ for 7 days and colonies were enumerated.

Harvest of ¼ of the culture is repeated on day 14, day 21, and day 28.

Figure 10:
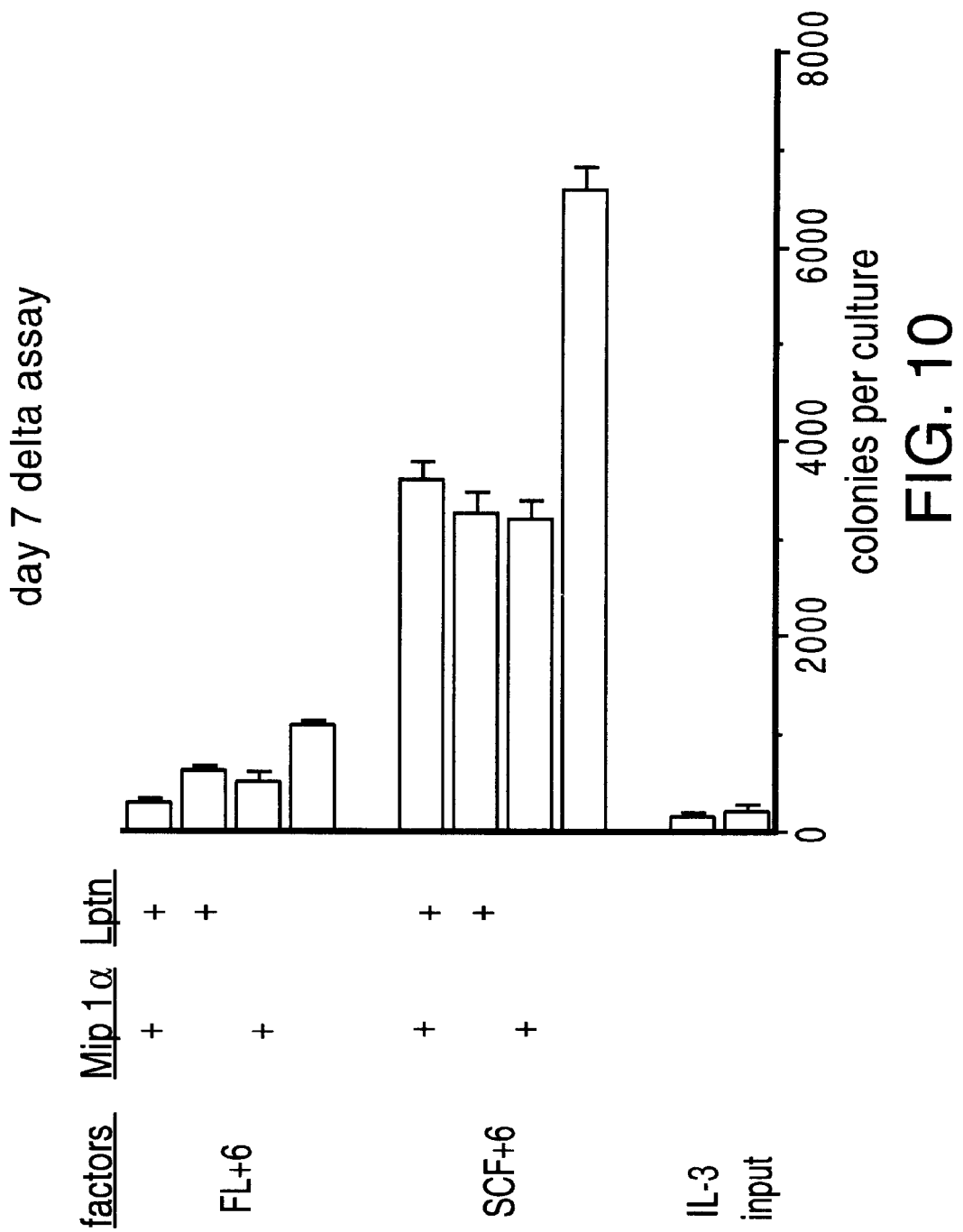
Figure 11:
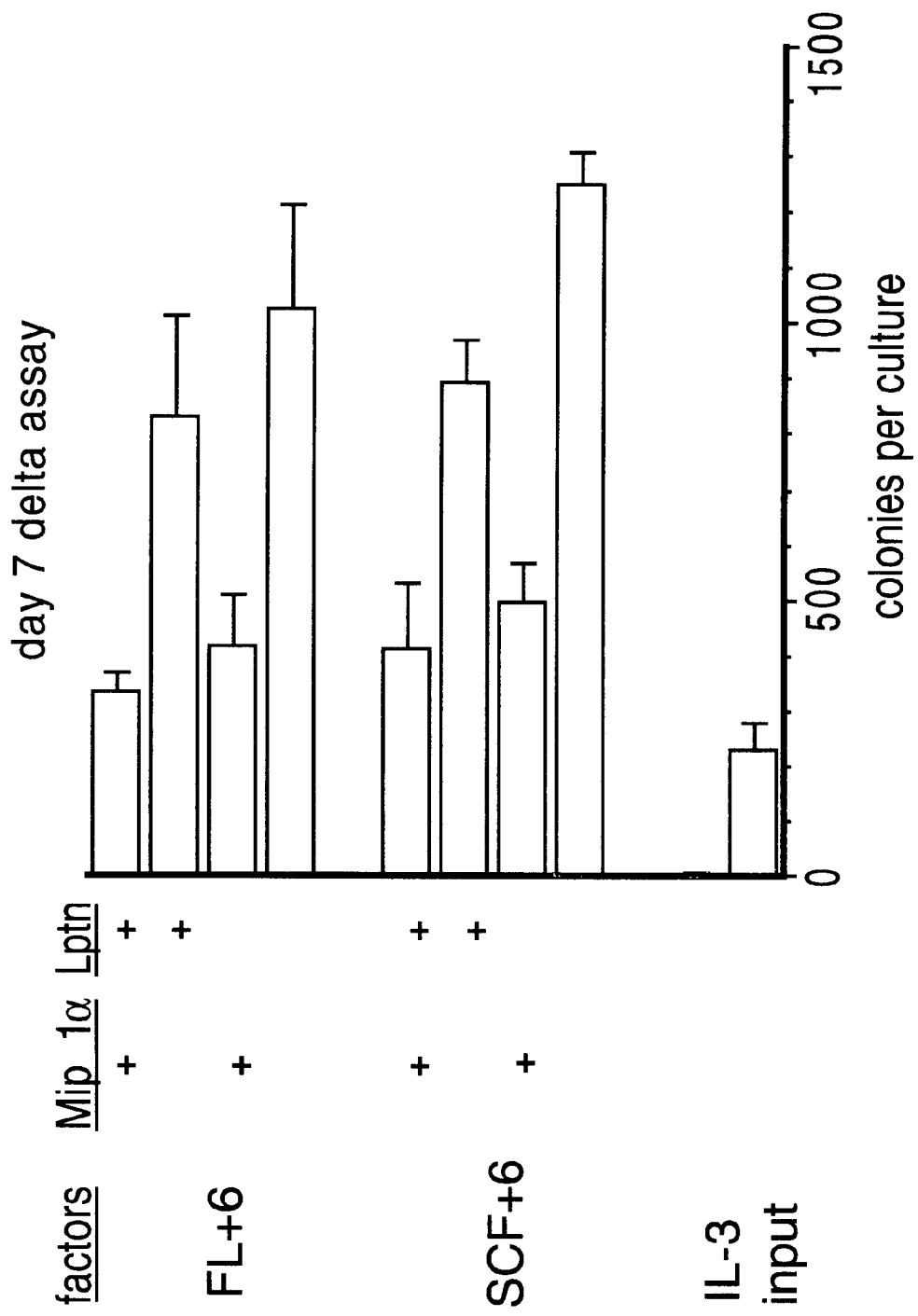

The effects of lymphotactin, alone or in combination with MIP-1α, Flt3 ligand, Stem Cell Factor, IL-6, and/or IL-3 are shown in FIGS. 10 (day 7), 11 (day 14), and 12 (day 21). These data show that lymphotactin, in combination with other factors, will have the effect of preventing hematopoietic stem cell from entering cycle and producing colonies at early time points, e.g., day 7, but will allow later colony formation, e.g., day 21. This data indicates the ability of lymphotactin to protect hematopoietic stem cells from damage by chemotherapeutic reagents by preventing their entry in cycle and the resultant cellular proliferation and differentiation for up to 21 days. The colony formation seen at day 21 indicates that the progenitors remained quiescent rather than dying during the initial culture period.

All references cited herein are incorporated herein by reference to the same extent as if each individual publication or patent application was specifically and individually indicated to be incorporated by reference.

Many modification an variations of this invention can be made without departing from its spirit and scope, as will be apparent to those skilled in the art. The specific embodiments described herein are offered by way of example only, and the invention is to be limited only by the terms of the appended claims, along with the full scope of the equivalents to which such claims are entitled.

Although the present invention has been described in some detail by way of illustration and example for purposes of clarity and understanding, it will be recognized that certain changes and modifications may be practiced within the scope of the claims.

What is claimed is:

1. A method of reducing allogeneic reaction from tissue transplant in a mammal, comprising a step of administering an amount of an antagonist of mammalian lymphotactin effective to reduce allogeneic reaction from tissue transplant to said mammal.

2. The method of claim 1, wherein said antagonist comprises an antigen binding site from an antibody which neutralizes mouse lymphotactin.

3. The method of claim 2, wherein said antibody is administered:
   a) at a dose of about 1–10 mg/kg body weight; or
   b) at about 10 to about 100 µg per milliliter of patient sera.

4. The method of claim 1, wherein said tissue is an organ.

5. The method of claim 1, wherein said antagonist reduces the influx of NK or CTL cells to said tissue.

6. The method of claim 1, wherein said tissue is an organ transplant, or bone marrow transplant.

7. A method of reducing migration of NK cells or T cells in a mammal comprising administering an antagonist to mammalian lymphotactin effective to reduce migration of NK cells or T cells in a mammal.

8. The method of claim 7, wherein said antagonist is an antibody or antibody fragment that specifically binds to mammalian lymphotactin.

* * * * *